United States Patent
Tchirikov

(10) Patent No.: US 9,339,633 B2
(45) Date of Patent: May 17, 2016

(54) BALLOON CATHETER SYSTEM FOR DRAINING FLUIDS FROM HOLLOW ORGANS, BODY CAVITIES OR CYSTS AND/OR FOR SUPPLYING MEDICATION

(75) Inventor: Michael Tchirikov, Halle (DE)

(73) Assignee: Universitatsmedizin der Johannes Gutenberg Universitat Mainz, Mainz (DE)

( * ) Notice: Subject to any disclaimer, the term of this patent is extended or adjusted under 35 U.S.C. 154(b) by 519 days.

(21) Appl. No.: 13/703,581

(22) PCT Filed: Jun. 8, 2011

(86) PCT No.: PCT/EP2011/002803
§ 371 (c)(1),
(2), (4) Date: Jan. 21, 2013

(87) PCT Pub. No.: WO2011/154128
PCT Pub. Date: Dec. 15, 2011

(65) Prior Publication Data
US 2013/0123622 A1    May 16, 2013

(30) Foreign Application Priority Data
Jun. 11, 2010  (DE) .......................... 10 2010 023 438

(51) Int. Cl.
*A61M 25/00* (2006.01)
*A61M 25/10* (2013.01)
*A61M 25/02* (2006.01)
(Continued)

(52) U.S. Cl.
CPC ............ *A61M 25/10* (2013.01); *A61M 25/0017* (2013.01); *A61M 25/02* (2013.01); *A61M 27/002* (2013.01); *A61M 31/005* (2013.01); *A61M 27/008* (2013.01); *A61M 2025/0063* (2013.01); *A61M 2025/0233* (2013.01); *A61M 2027/004* (2013.01); *A61M 2210/145* (2013.01)

(58) Field of Classification Search
CPC ............... A61M 2025/1061; A61M 25/10185; A61M 25/10186; A61M 25/10184
See application file for complete search history.

(56) References Cited

U.S. PATENT DOCUMENTS 3,577,992 A * 5/1971 Merry et al. ............... 604/99.02
3,860,006 A   1/1975 Patel
(Continued)

FOREIGN PATENT DOCUMENTS

DE            2752702       11/1977
DE            3214905       12/1982
(Continued)

*Primary Examiner* — Leslie Deak
*Assistant Examiner* — Kai Weng
(74) *Attorney, Agent, or Firm* — McHale & Slavin, P.A.

(57) ABSTRACT

The present invention relates to a balloon catheter system for draining and/or supplying fluid from/into hollow organs, body cavities or cysts, comprising a conduit catheter with an open distal end, a hollow needle guided in a separate guide conduit and a balloon surrounding the catheter stem at the distal end of the conduit catheter. The conduit catheter with the hollow needle can be inserted from outside into the hollow organ via a guide catheter, into the body cavity or cyst, the balloon can be filled with filling medium via the hollow needle through an opening formed in the guided duct and provided in the lumen of the balloon, and it can be fixed in the hollow organ, body cavity or cyst. The hollow needle can be removed from the guide duct after filling the balloon. The balloon and the conduit catheter remain in the hollow organ, body cavity or cyst.

17 Claims, 3 Drawing Sheets

(51) Int. Cl.
*A61M 27/00* (2006.01)
*A61M 31/00* (2006.01)

(56) References Cited

U.S. PATENT DOCUMENTS

| | | | |
|---|---|---|---|
| 4,474,569 A | 10/1984 | Newkirk | |
| 4,475,898 A | 10/1984 | Brodner et al. | |
| 4,531,933 A | 7/1985 | Norton et al. | |
| 5,201,724 A * | 4/1993 | Hukins et al. | 604/265 |
| 7,470,247 B2 | 12/2008 | Aliski et al. | |
| 2003/0195456 A1 | 10/2003 | Robertson | |
| 2005/0080399 A1* | 4/2005 | Bolmsjo et al. | 604/509 |
| 2007/0276466 A1* | 11/2007 | Lavelle | A61F 2/04 623/1.22 |
| 2008/0147001 A1* | 6/2008 | Al-Marashi et al. | 604/103.04 |

FOREIGN PATENT DOCUMENTS

| | | |
|---|---|---|
| DE | 102010023438.9 | 6/2010 |
| WO | WO2005025665 | 3/2005 |
| WO | WO2011063094 | 5/2011 |

* cited by examiner

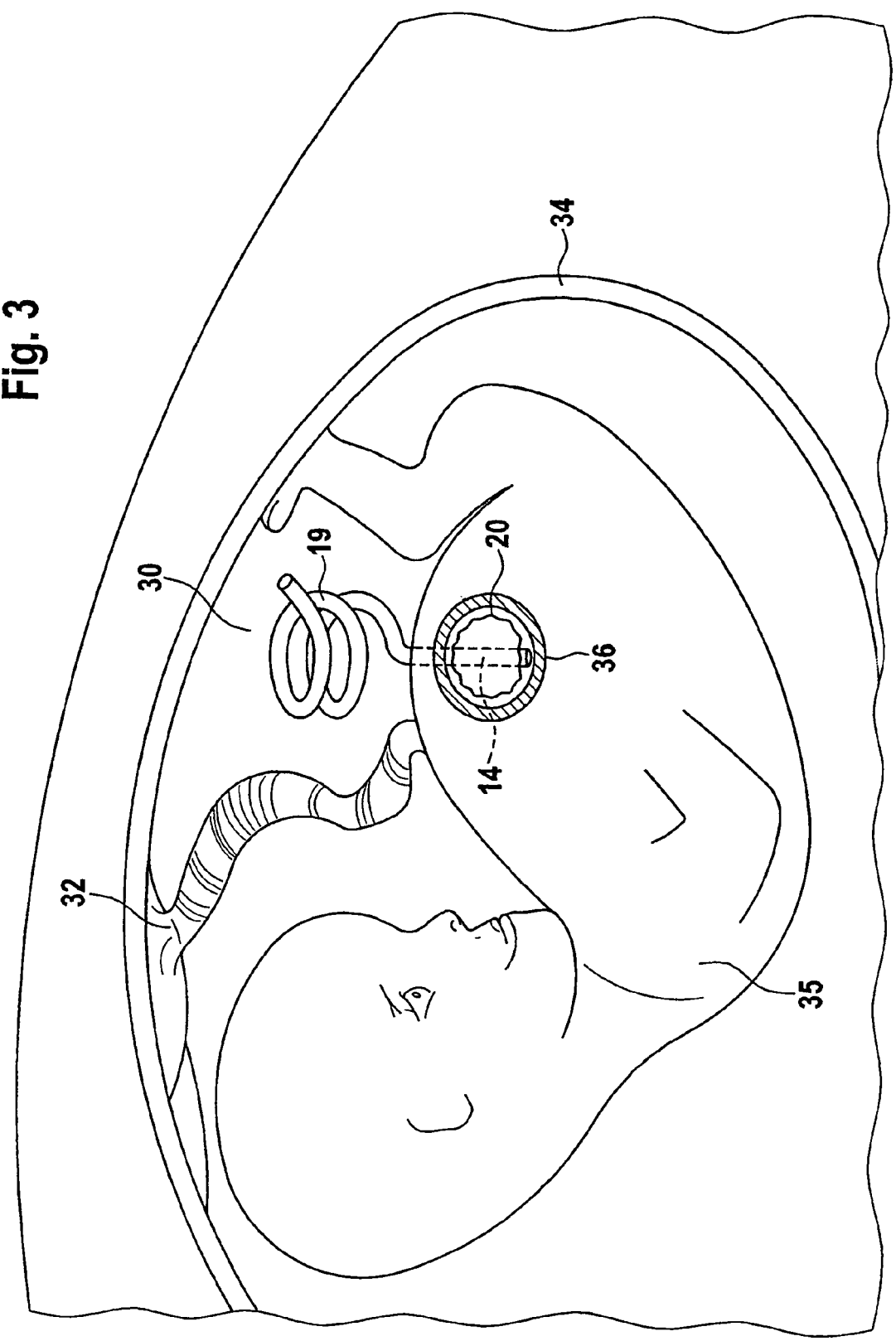

BALLOON CATHETER SYSTEM FOR DRAINING FLUIDS FROM HOLLOW ORGANS, BODY CAVITIES OR CYSTS AND/OR FOR SUPPLYING MEDICATION

CROSS REFERENCE TO RELATED APPLICATIONS

This is a national stage filing in accordance with 35 U.S.C. §371 of PCT/EP2011/002803, filed Jun. 8, 2011, which claims the benefit of the priority of German Patent Application No. 102010023438.9, filed Jun. 11, 2010, the contents of each are incorporated herein by reference.

DESCRIPTION

A balloon catheter system for draining fluids from hollow organs, body cavities or cysts and/or for supplying medication.

FIELD OF THE INVENTION

The present invention relates to a balloon catheter system for draining fluids from hollow organs, body cavities or cysts and/or for supplying medication, in accordance with the preamble of Claim 1. The invention also relates to the use of the balloon catheter system for treating a prenatal infravesical foetal obstruction, a congenital cystic lung malformation, hydronephrisis, or hydrocephalus. The balloon catheter system is also suitable for suprapubic applications in adults.

DESCRIPTION OF THE BACKGROUND ART

The draining of fluids from body cavities, hollow organs, cysts or tumour constitutes a serious problem in unborn foetuses or in adults. An example of such a symptom in hollow organs is obstructive uropathies which result in urinary stasis owing to an outflow obstruction in the discharging urinary tracts. Prenatal infravesical foetal obstruction represents a very frequent symptom of obstructive uropathy in foetuses. In some cases, a terminal insufficiency or a pulmonary hypoplasia in the case of anhydramnia develops as a consequence of an infravesical obstruction in new-born babies, as well as subsequently in girls and boys. Many children born with such a defect become dialysis-dependent and in the long term exhibit renal insufficiency. In the worst case, an infravesical foetal obstruction leads to the death of the child.

The cause of an infravesical obstruction is often excessively high pressure in the sphincter region or urethral flap, whereby the urine is only evacuated when the bladder is overfilled, i.e. when the pressure in the bladder is higher than the outlet resistance of the sphincter. This phenomenon is also termed bladder overflow.

Only in rare cases, is the spiral-shaped "Michael Harrison" catheter used in the event of a prenatal infravesical obstruction, which is known for this purpose. The positioning of the Harrison catheter in the urinary bladder of the foetus is extremely complicated and owing to the extremely thick guide needle there is a high risk of premature rupture of the bladder and the triggering of a miscarriage or injury to the patient or foetus. Moreover, the problem arises that the foetus removes the catheter in the womb owing to its play instinct so that a complicated reimplantation of the catheter is necessary. This is the case in particular with the hitherto used but non-fixed pigtail catheter. The latter is not secured in the urinary bladder of the foetus and is often removed by the baby. A reimplantation of the catheter is thereby necessary, which constitutes another surgical intervention for the patient and thus the risk of a miscarriage. In many cases, the symptom remains untreated and, unfortunately, does not lead to the desired treatment result. Upon application of the Harrison catheter, the urinary bladder is permanently evacuated, which leads to bladder hypoplasia. This is unsatisfactory.

The fixing of a catheter via a balloon in the urinary bladder through the urethra is known per se (Foley catheter). Foley catheters have an elastic, inflatable balloon which surrounds the stem of the catheter near to its front end. In the non-inflated state, the balloon is closely adjacent the stem so that it impedes only to a very small extent the insertion of the stem through urethra until an outlet opening at the front end of the stem reaches the desired length, e.g. in the bladder. After the catheter has been brought into the correct position in this way, the balloon is inflated with a fluid medium via a special inflation duct passing through the stem. In the inflated state of the balloon, the inflation conduit is closed so as to prevent removal of the catheter. The catheter remains in the urinary bladder for several weeks. Since the urinary bladder of a foetus in the womb of a expectant mother is not at all accessible or only with difficulty, the application of a Foley catheter, as disclosed in DE 27 52 702 A, is entirely unsuitable for the treatment of a prenatal infravesical foetal obstruction.

DE 32 14 905 A1 discloses a catheter for suprapubic application, which is provided with a puncture needle and a catheter tube receiving the puncture needle in its lumen. The catheter has a stabiliser, which arranged for fastening to the patient's body, with a plate which extends on two opposite sides of the catheter tube and which is slidably mounted by means of an opening on the catheter tube, whereby the stabiliser can be locked by an associated locking device at a respective desired location on the catheter tube. Owing to its construction, this catheter would also be unsuitable for the treatment of a prenatal infravesical foetal obstruction.

Hitherto, the occurrence of renal insufficiency and the other above-mentioned risks have been taken into consideration in the event of an infravesical obstruction, because the danger of infection, premature birth or miscarriage would be too great with the use of the Harrison catheter.

SUMMARY OF THE INVENTION

Against this background, it is the object of the present invention to provide a catheter for draining fluids from hollow organs, body cavities or cysts and/or for supplying medication, which obviates the drawbacks of the hitherto used Harrison catheter and, in particular, is suitable for the treatment of a prenatal infravesical foetal obstruction or other medical conditions with abnormal accumulation of fluid in cavities such as prenatal infravesical foetal obstruction, a congenital cystic lung malformation, hydronephrisis, or hydrocephalus.

This object is achieved by a balloon catheter system having the technical features of Claim 1.

Preferred embodiments are set out in the sub-claims.

The balloon catheter system according to the invention comprises a hollow conduit catheter open at the ends and with a hollow needle guided in a guide duct separated from the large-volume conduit lumen of the conduit catheter, and with a balloon surrounding the catheter stem at the distal end of the conduit catheter. The conduit catheter with the hollow needle can be inserted from outside into a hollow organ, a body cavity or a cyst, in particular into the urinary bladder of a foetus, through the uterus wall and the balloon can be filled with a filling medium via the hollow needle by way of an opening formed on the guide duct of the hollow needle and disposed in the lumen of the balloon.

Via the lumen of the conduit catheter, at the distal open end of the conduit catheter the fluid is directed from the hollow organ, the body cavity or the cyst (e.g. urine from the urinary bladder of the foetus) outwards (e.g. into the amniotic cavity). Preferably, the proximal end of the conduit catheter is in the form of a pigtail catheter. The balloon preferably surrounds the conduit catheter so as to prevent any outlet of fluid from the balloon. The catheter is securely fixed by the filled balloon inside the hollow organ, body cavity or cyst, e.g. the urinary bladder of a foetus, thereby preventing removal of the conduit catheter at the pigtail by the foetus. The hollow needle can be removed from the guide duct of the conduit catheter after the balloon has been filled with the filling medium. Preferably, an additional, preferably reinforced guide catheter is guided in the conduit catheter. The system can thereby be introduced more readily into the hollow organ, body cavity or cyst. The pigtail (i.e. the loop-shaped catheter structure) at the proximal end of the conduit catheter is formed only when the guide catheter is pulled from the conduit catheter, whereupon the balloon inflated by the filling medium remains in the hollow organ, body cavity or cyst, e.g. the urinary bladder of the foetus. In a preferred embodiment, the balloon catheter system is characterised in that the balloon neck of the balloon and/or the guide duct of the conduit catheter is provided with a non-return valve to prevent deflation of the balloon and thus the outlet of filling medium. The non-return valve may be small plate which is disposed in the guide duct and closes the guide duct of the conduit catheter upon formation of the pigtail. Any other suitable valve, which is disposable and closable within the guide duct such as an elastic membrane is also encompassed by the present invention.

The valve can be designed to be controllable from the outside, e.g. by using an electronically or magnetically adjustable valve. In order to provide for the possibility to deflate the balloon, the valve can be opened in one direction to withdraw liquid from the balloon. Alternatively, the valve can be designed to work in the other direction, or in both directions, i.e. to inflate or deflate the balloon with or from liquid, respectively.

In another preferred embodiment, the deflation of the balloon is prevented by a fully or partially formable or elastic guide duct, which can be closed upon filling the balloon with filling medium. Preferably, the closing of the guide duct is achieved by an internal membrane or flap that is arranged within the guide duct. The membrane or flap undergoes a folding conformation following withdrawal of the hollow needle from the duct, thereby closing the duct channel.

In an alternative embodiment, the guide duct can be closed by using a shrinkable guide duct material. This can be achieved, for instance, by a preformed guide duct made of synthetic material. The hollow needle is guided through the guide duct to fill the balloon with filling medium, while the guide duct remains in extended condition. Upon filling the balloon and subsequent removal of the hollow needle, the guide duct shrinks and thereby closes the channel. It is not necessary that the whole guide duct is made of shrinkable material. In one embodiment only a part or portion of the guide duct is shrinkable.

Alternatively, the guide duct can be closed by using a glue or gum that is inserted into the duct following filling the balloon with filling medium. Preferably, a biogenous or organic glue/gum is used for closing the guide duct.

After birth, the balloon can either be deflated by opening the non-return valve, removing the guide duct, or by tapping the balloon, e.g. with a needle.

One application sector of the balloon catheter system according to the invention is the treatment of a prenatal infravesical obstruction. According to the invention, for this purpose the conduit catheter is introduced with the hollow needle guided in the guide duct and with the deflated balloon arranged at the distal end, initially, through the uterus wall to the foetus and, finally, into the latter's urinary bladder. The deflated balloon then surrounds the stem of the conduit catheter. It is possible to use for the insertion of the balloon catheter system a hollow needle of slightly larger diameter which, however, is markedly smaller in diameter than the hitherto used Harrison catheter. Once the conduit catheter with the balloon has been inserted into the urinary bladder of the foetus, it can be inflated by supplying the filling medium via the hollow needle guided in the separate guide duct and, depending on the application, this is preferably physiological saline solution, water or contrast medium. In this case, the balloon envelope is applied against the inner urinary bladder wall and keeps the latter under tension. An adjustable balloon that is able to increase its size during growth of the foetus, and hence its urinary bladder, is preferred.

Depending on the development of the foetus and the clinical situation, it can be necessary to insert different balloon sizes during the different growth stages of the foetus. In such an embodiment, a balloon of the respective size is inserted via the catheter system of the invention into the urinary bladder of the foetus while at the same time the previous balloon is removed.

In a preferred embodiment, the envelope of the balloon is made of a semipermeable membrane. The balloon is filled with a hypotonic solution as filling medium in order to adapt to the different growth stages of the foetus. The hypotonic solution results in a steady but slow increase of the balloon size during growth of the foetus by attracting liquid from the cavity of the urinary bladder into the lumen of the balloon.

The urine is drained outwards from the urinary bladder of the foetus via the open distal end of the conduit catheter. The back flow of fluid from the balloon is preferably prevented by the non-return valve. In a first embodiment, the non-return valve is situated on the balloon neck of the balloon. In another embodiment, the non-return valve is situated in the opening of the guide duct and closes it after the filling of the balloon has taken place. In a further embodiment, the non-return valve is situated in the guide duct of the hollow needle. An arrangement of this type is advantageous in particular in the proximal part of the conduit catheter, in which the above-mentioned pigtail structure is formed after removal of the guide catheter. The non-return valve closes the guide duct as a result of the loop formation of the conduit catheter.

Preferably, the non-return valve consists of the same material as the balloon envelope or the conduit catheter, preferably of a biodegradable material, for example biodegradable latex.

Alternatively, a shrinkable synthetic material can be used instead of a non-return valve. The shrinkable material can be part of the guide duct, being able to close the channel when the hollow needle is withdrawn.

As a result of the inflation of the balloon, the catheter is fixed in the urinary bladder and prevents decompression of the urinary bladder and thus bladder hypoplasia. Another advantage is that the insertion and fixing of the catheter is visible via ultrasound, thereby facilitating the guiding and fixing of the catheter and, ultimately, the risk of injury to the foetus and mother is also reduced.

For draining fluid from the hollow organ, body cavity or cyst, for example urine from the urinary bladder of the foetus, or for supplying medication, in another embodiment at least one further lumen for supplying medication or for draining urine from the urinary bladder of the foetus is provided in the lumen of the catheter. In one embodiment, the lumen can be formed in the conduit catheter itself. In a preferred embodiment, the proximal end of the conduit catheter can be connected to a port system implanted under the skin. In this way, it is possible for fluid to be drained and supplied transcutaneously outside the body.

By using a (bio) degradable material, the balloon and/or the conduit catheter (depending on the form of application) dissolves within a few weeks or months so that another surgical intervention for its removal is no longer necessary.

The insertion of the conduit catheter and the guide catheter guided therein is effected via a markedly thinner hollow needle compared to the Harrison catheter, preferably an 18 G, or smaller needle, whereby there danger of injury and pain for the patient is decreased during the implantation. The above-mentioned drawbacks in using the unacceptably thick Harrison catheter and its technically complicated implantation are substantially diminished by the balloon catheter system according to the invention.

The conduit catheter has in its guide duct an opening through which the balloon is inflated with filling medium. The end of the hollow needle guided in the guide duct is preferably blunt so that it can be guided without damage through the optional non-return valve disposed in the guide duct. Additionally, the hollow needle fulfills the function of reinforcing the conduit catheter. By using a very thin conduit catheter, the acceptability of a puncture for the patient is more readily assured than with the hitherto used the very thick Harrison catheter. Accordingly, this results in a lower danger of injury and pain which are caused by the puncture. Moreover, the balloon makes possible a secure and atraumatic fixing and is uncomplicated in its application. After positioning has taken place, the removal of the optional guide catheter from the guide catheter is effected. Preferably, the guide catheter is a guide wire, it being possible for all other known guide structures to be used. One aim of the guide catheter lies in its function of reinforcing the loop-shaped pigtail part of the conduit catheter.

In addition to the aforementioned bladder hypoplasia, the application of the balloon catheter system in a suprapubic urine drain reduces the occurrence of a pulmonary hypoplasia with anhydramnia and the occurrence of renal insufficiency in the new-born baby. Therefore, the balloon catheter system according to the invention is particularly suitable for the treatment of a prenatal infravesical obstruction.

An important advantage of the balloon catheter system according to the invention lies in that it can be fixed in the hollow organ, body cavity or cyst and the conduit catheter connected to the balloon cannot be withdrawn. Another advantage of the balloon catheter system according to the invention lies in that the balloon retains its volume inside the hollow organ, body cavity or cyst even if the catheter is removed. Compared to the hitherto used Harrison catheter, the balloon catheter system according to the invention is of markedly smaller diameter. It is especially advantageous that collapse of the hollow organ is prevented by the fixing of the balloon in the hollow organ and the inflation with a filling medium.

In a preferred embodiment, the hollow organ is the urinary bladder of a foetus and the balloon catheter system is utilised in the treatment of a prenatal infravesical obstruction. Owing to its positioning in the urinary bladder of the foetus, the balloon inflated with the filling medium prevents bladder hypoplasia, whereas at the same time the urine produced by the foetus can be drained via the conduit catheter into the amniotic cavity. By fixing the balloon in the urinary bladder, it is also possible to prevent removal of the drain catheter even if the baby pulls on the catheter within the ambit of its play instinct.

The balloon catheter system according to the invention is generally suitable for draining fluids from hollow organs, body cavities or cysts. In addition, the supply of medication, depending on the type of application, is also possible. Moreover, the balloon catheter system according to the invention is also suitable for the treatment of a congenital cystic lung malformation, renal stasis or hydrocephalus.

BRIEF DESCRIPTION OF THE DRAWINGS

Preferred embodiments will be illustrated in the following drawings, wherein

FIG. 3 shows the application of the balloon catheter system to the treatment of a prenatal infravesical obstruction in a foetus.

ONE POSSIBLE WAY TO CARRY OUT THE INVENTION

Figure 1:
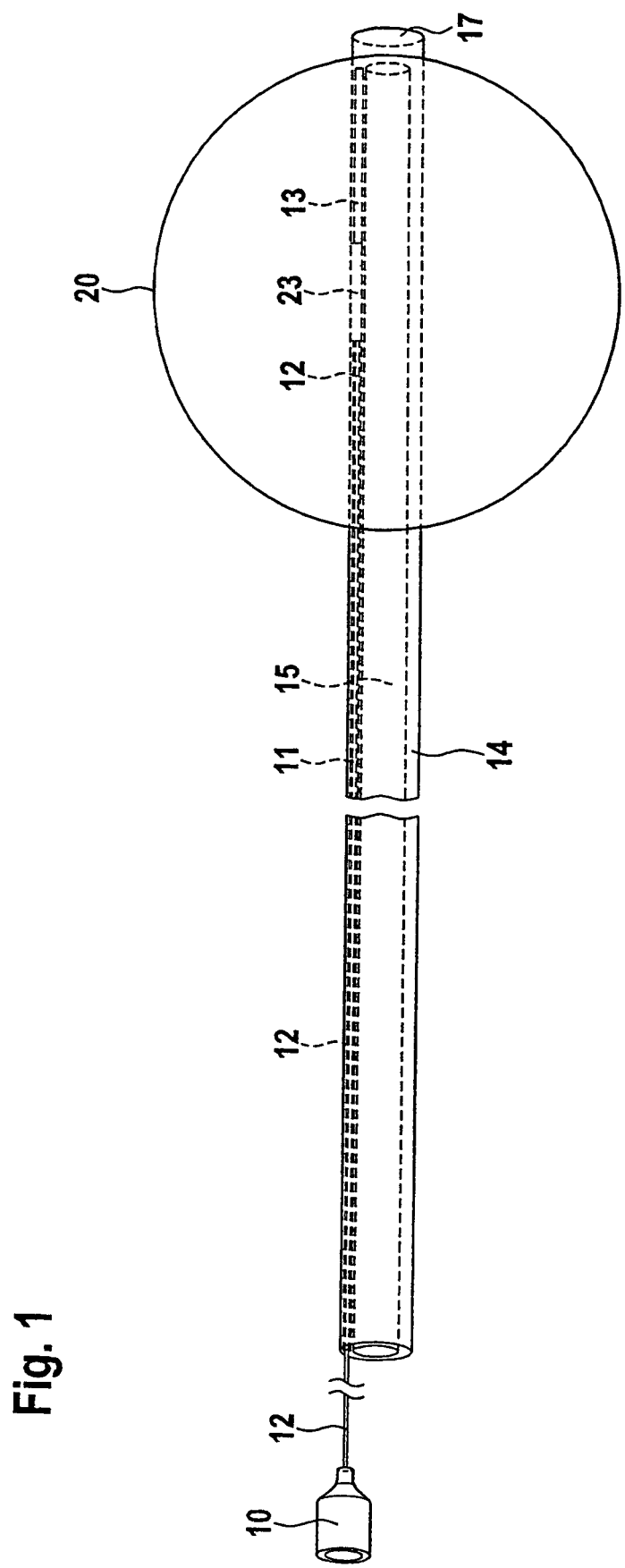
FIG. 1 shows an isometric illustration of the balloon catheter system according to the invention with inflated balloon.

FIG. 1 shows the construction of an embodiment of the balloon catheter system according to the invention, as used for the treatment of a prenatal infravesical obstruction. It comprises a conduit catheter 14 with a hollow needle 12 which is guided in the conduit catheter in a separate guide duct 13 and to the proximal end of which an adapter 10 is connected. By way of the adapter 10 it is possible to supply a filling medium for inflating the balloon 20 arranged at the distal end 17 of the conduit catheter 14. The guide duct 13 is a separate duct formed in the lumen of the conduit catheter 14 and is fluidtightly sealed from the large-volume lumen of the conduit catheter 14. The distal end 17 of the conduit catheter 14 is open and serves to drain urine from the urinary bladder of the foetus. An additional guide catheter 15 is provided in the conduit catheter 14 so as to guide and position it. The proximal end of the conduit catheter 14 is preferably in the form of a pigtail, i.e. after removal of the guide catheter 15 it forms a loop-like structure. The hollow needle 12 is open at the end. The guide duct 13 and thus the outer skin of the conduit catheter 14 has an opening 23 which is disposed in the vicinity of the lumen of the balloon 20 and through which the filling medium is admitted for inflating the balloon 20.

Physiological saline solution is preferably used the filling medium but, depending on the application, a hyptonic solution, water or contrast medium can also be used for filling the balloon 20. After the filling of the balloon 20, the hollow needle 12 is withdrawn from the guide duct 13. Back flow of the filling medium from the balloon 20 is prevented by way of a non-return valve 11 disposed in the guide duct 13.

Figure 2:
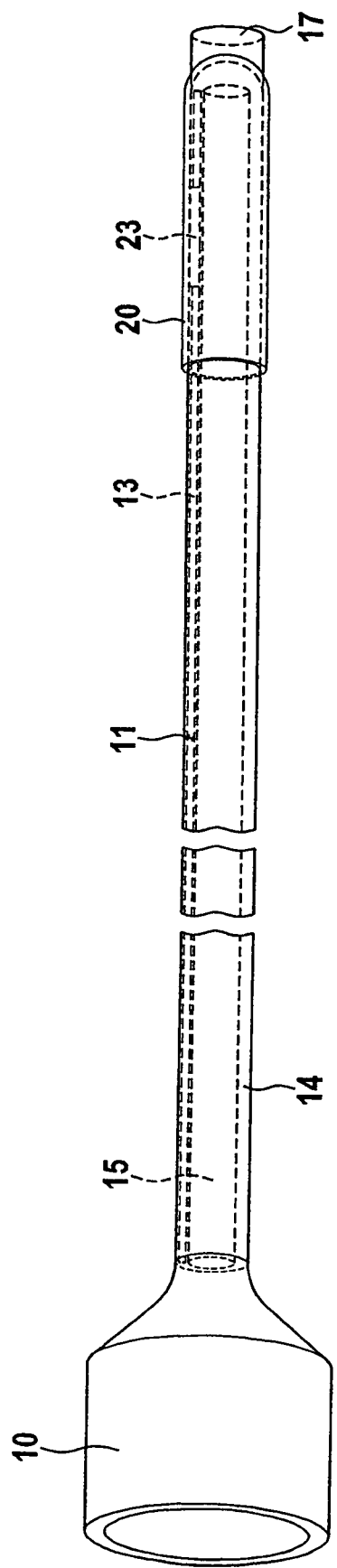
FIG. 2 shows a detailed illustration of the balloon catheter with deflated balloon.

FIG. 2 shows an embodiment in which the balloon surrounds the stem of the conduit catheter 14 in the deflated state, whereas the distal end 17 of the conduit catheter 14 projects from the balloon 20. The non-return valve 11 is visible in the guide duct 13 of the conduit catheter 14. The guide catheter 15 extends in the conduit catheter 14.

FIG. 3 shows an application of the balloon catheter system according to the invention, in which the treatment of a prenatal infravesical obstruction. The conduit catheter 14 is inserted into the urinary bladder 36 of a foetus 36 via the uterus wall 34. Subsequently, filling medium for filling the balloon 20 is introduced via the hollow needle 12 (not shown). The urine of the foetus is drained into the amniotic cavity 30 via the lumen of the conduit catheter 14. The proximal end of the conduit catheter 14 is configured as a loop-shaped pigtail catheter and leads into the amniotic cavity 30. Moreover, the umbilical cord 32 of the foetus 35 is also visible.

The invention claimed is:

1. A balloon catheter system for draining and/or supplying fluid from/into hollow organs, body cavities or cysts, comprising:
    a conduit catheter having an elongated body having an outer surface, said elongated body having an open proximal end and terminating in an open distal end configured to drain fluids from hollow organs, body cavities or cysts and/or for supplying medication, said proximal end containing a portion which traverses between a linear configuration in a first orientation and a non-linear configuration having at least one looped portion in a second orientation, said elongated body having a hollow needle guide duct separated from an interior lumen of said conduit catheter, said hollow needle guide duct having an opening that extends through said outer surface of said conduit catheter body and which is surrounded by an interior of an inflatable balloon;
    a removable hollow needle having a body sized and shaped to extend within and slidably enage said hollow needle guide duct, said hollow needle body having an opening which when inserted within said hollow needle guide duct rests at or near said hollow needle guide duct opening;
    said inflatable balloon affixed to a portion of the conduit catheter;
    a valve configured to prevent deflation of said balloon, said valve located in the neck of the balloon or the hollow needle guide duct of the conduit catheter, and
    a guide catheter having an elongated body of sufficient length to extend within and be positioned within the lumen of the conduit catheter thereby forming a coaxial alignment;
    characterised in that the conduit catheter with the removable hollow needle in the hollow needle guide duct can be inserted from outside into the hollow organ, the body cavity or cyst via the guide catheter provided in the conduit catheter, the balloon can be filled with filling medium via the removable hollow needle through said opening formed in the hollow needle guide duct and provided in the lumen of the balloon, wherein the balloon can be fixed in the hollow organ, body cavity or cyst and the hollow needle can be removed from the hollow needle guide duct of the conduit catheter after filling of the balloon, whereas the balloon and the conduit catheter remain in the hollow organ, body cavity or cyst.

2. The balloon catheter system according to claim 1, characterised in that the conduit catheter is configured to fit into a urinary bladder of a foetus, wherein the conduit catheter with the guide catheter and the hollow needle can be inserted through the uterus wall into the urinary bladder of a foetus and can be fixed in the urinary bladder of the foetus, and the hollow needle can be removed from the conduit catheter after the filling of the balloon with the filling medium, whereas the conduit catheter remains with the balloon in the urinary bladder.

3. The balloon catheter system according to claim 1, characterised in that the valve is a non-return valve.

4. The balloon catheter system according to claim 1, characterised in that at least a portion of the conduit catheter is provided with a shrinkable synthetic material or an internal membrane.

5. The balloon catheter system according to claim 1, characterised in that the balloon and/or the conduit catheter consists of a biodegradable material.

6. The balloon catheter system according to claim 1, characterised in that the filling medium is physiological saline solution, hypotonic solution, water or contrast medium.

7. A method for treatment of prenatal infravesical foetal obstruction, congenital cystic lung malformation, hydronephrisis, or hydrocephalus comprising the steps of inserting a balloon catheter system according to claim 1 into a hollow organ, body cavities or cysts which requires fluid drainage or introduction of medication therein; and draining said fluid within said hollow organ, body cavities or cysts or supplying said medication into said hollow organ, body cavities or cysts.

8. The balloon catheter system according to claim 2, characterised in that the balloon and/or the conduit catheter consists of a biodegradable material.

9. The balloon catheter system according to claim 3, characterised in that the balloon and/or the conduit catheter consists of a biodegradable material.

10. The balloon catheter system according to claim 4, characterised in that the balloon and/or the conduit catheter consists of a biodegradable material.

11. The balloon catheter system according to claim 2, characterised in that the filling medium is physiological saline solution, hypotonic solution, water or contrast medium.

12. The balloon catheter system according to claim 3, characterised in that the filling medium is physiological saline solution, hypotonic solution, water or contrast medium.

13. The balloon catheter system according to claim 4, characterised in that the filling medium is physiological saline solution, hypotonic solution, water or contrast medium.

14. The balloon catheter system according to claim 5, characterised in that the filling medium is physiological saline solution, hypotonic solution, water or contrast medium.

15. A method for treatment of prenatal infravesical foetal obstruction comprising the steps of:
    using a balloon catheter system according to claim 1 for treatment of a prenatal infravesical foetal obstruction;
    inserting said conduit catheter, into a urinary bladder of said fetus, said distal end of said conduit catheter positioned within said urinary bladder of said fetus in a non-inflated state and at least a portion of said proximal end positioned outside of said fetal urinary bladder into an amniotic cavity;
    aligning said removable hollow needle inserted within said hollow needle guide duct to fill said balloon with said filling medium by positioning said hollow needle body opening at or near said hollow needle guide duct opening;
    inflating said balloon inside said fetal bladder by inserting said balloon filling medium into said hollow needle; and
    forming at least one looped portion positioned at the proximal end of said conduit catheter by removing said guide catheter from said inner lumen of said conduit catheter.

16. The method for treatment of prenatal infravesical foetal obstruction according to claim 15 further including the step of draining a fluid from said urinary bladder of said foetus.

17. The method for treatment of prenatal infravesical foetal obstruction according to claim 15 further including the step of supplying medication into said urinary bladder of said foetus.

\* \* \* \* \*